(12) United States Patent
Casas et al.

(10) Patent No.: US 8,148,144 B2
(45) Date of Patent: Apr. 3, 2012

(54) PCRYPTORNAI

(75) Inventors: Jon Ander Ochoa de Eribe Casas, Chiba (JP); Susumu Kawamoto, Chiba (JP)

(73) Assignee: National University Corporation Chiba University, Chiba (JP)

( * ) Notice: Subject to any disclaimer, the term of this patent is extended or adjusted under 35 U.S.C. 154(b) by 0 days.

(21) Appl. No.: 12/410,748

(22) Filed: Mar. 25, 2009

(65) Prior Publication Data

US 2009/0258366 A1 Oct. 15, 2009

Related U.S. Application Data

(60) Provisional application No. 61/039,906, filed on Mar. 27, 2008.

(51) Int. Cl.
*C12N 15/63* (2006.01)
*C12N 1/15* (2006.01)

(52) U.S. Cl. ............... 435/320.1; 536/23.1; 435/254.11

(58) Field of Classification Search ..................... None
See application file for complete search history.

(56) References Cited

FOREIGN PATENT DOCUMENTS

CN 1242063 C * 2/2006

OTHER PUBLICATIONS

Luo et al. (Gene, 2007, vol. 395, pp. 160-169).*
Liu et al. (Genetics, 2002, vol. 160, pp. 463-470).*

* cited by examiner

*Primary Examiner* — Celine Qian
(74) *Attorney, Agent, or Firm* — Kilyk & Bowersox, P.L.L.C.

(57) ABSTRACT

A vector developed to transform fungi can be used to study the expression of a gene of interest. The vector can provide for the expression of signal proteins in fungi that can be observed and/or monitored. The vector can be used to investigate the effects of RNA interference on a gene of interest in pathogenic fungi. Systems and methods of using the vector are provided.

11 Claims, 9 Drawing Sheets

First Round Fusion PCR reaction
L1: 500bp molecular ladder
L2: alpha-a product
L3: alpha-b product (Actin promoter)
L4: alpha-c product
L5: beta-a product
L6: beta-b product (Actin promoter)
L7: beta-c product Second Round Fusion PCR reaction
L1: 500bp molecular ladder
L2: control using p2FP-RNAi template
L3: 2alpha PCR fusion 1
L4: 2alpha PCR fusion 2
L5: 2alpha PCR fusion 3 (3% DMSO)
L6: control using p2FP-RNAi template
L7: 2beta PCR fusion 1
L8: 2beta PCR fusion 2
L9: 2beta PCR fusion 3 (3% DMSO)

PCRYPTORNAI

This application claims the benefit under 35 U.S.C. §119 (e) of prior U.S. Provisional Patent Application No. 61/039,906, filed Mar. 27, 2008, which is incorporated in its entirety by reference herein.

FIELD OF THE INVENTION

This invention relates generally to the field of biology and chemistry. More particularly, the invention is directed to a vector that can be used to study pathogenic fungi.

BACKGROUND OF THE INVENTION

As there was no vector available for the study of RNA interference (RNAi) in pathogenic fungi, there was a need for such a vector. A plasmid that can be used for the study of RNAi in mammalian cells is commercially available, p2FP-RNAi vector (Evrogen, Moscow, Russia). No such vectors, however, have been developed that are general enough to embrace the study of RNAi in pathogenic fungi using any genetic sequence of interest or gene of interest (GOI). A need exists for a vector that allows for the molecular investigation of pathogenic fungi using RNAi techniques.

SUMMARY OF THE INVENTION

The present invention relates to a vector developed to transform fungi. In particular, the vector can be used to investigate RNA interference in pathogenic fungi. In one or more embodiments, the vector can comprise a plasmid comprising a first signal protein gene sequence that codes for a first signal protein. The first signal protein sequence can be operably linked to a first promoter capable of controlling the expression of the first signal protein in fungi. In one or more embodiments, a desired GOI can be cloned into the plasmid such that the GOI will be tagged with the first signal protein. The GOI can be cloned, for example, into a 3' prime untranslated region (3'-UTR) of the first signal protein sequence. When transformed into a cell, the plasmid can produce a first signal protein mRNA comprising the 3'-UTR sequence of the GOI. In one or more embodiments, a plasmid comprising the GOI can be transfected into fungi and expression of the first signal protein can be observed and/or measured.

In one or more embodiments, the plasmid can further comprise a second signal protein gene sequence operably linked to a second promoter capable of controlling expression of the second signal protein in fungi. The second signal protein sequence can code for a protein that is distinguishable from the first signal protein.

In one or more embodiments, fungi transfected with a plasmid comprising a GOI can further be transfected with GOI sequence specific interfering RNA (siRNA). The GOI mRNA can be reduced by the cell's RNA-dependent Induced Silencing Complex (RISC), which can thus silence expression of both the cloned GOI and endogenous GOI sequences. In one or more embodiments, degradation of the cloned GOI mRNA sequence by RISC can also inhibit the translation of the first signal protein that is fused upstream of the GOI.

In one or more embodiments, the degradation of the cloned GOI mRNA sequence, and inhibited translation of the first signal protein, can produce a "shutter-like" effect, wherein cells being silenced will express the second signal protein, but not the first signal protein. On the other hand, control cells that have been transformed with a control plasmid, or that lack GOI siRNA, can express both the first signal protein and the second signal protein. This can be especially important in those sequences that are expressed in low basal profiles and are difficult to detect using standard Northern or Southern detection techniques, or in sequences that do not apparently contribute to the production of a clear phenotype.

One or more embodiments of the present invention can provide a novel tool that offers an advantage to scientists who wish to study RNA interference in fungi. One or more embodiments of the present invention can provide a definite product for commercial biotech companies.

Features and advantages of the present invention will become apparent from the following description. This description, which includes drawings and examples of specific embodiments, provide a broad representation of the invention. Various changes and modifications within the spirit and scope of the present invention will become apparent to those skilled in the art from this description and by practice of the invention. The scope of the present invention is not intended to be limited to the particular forms disclosed and the invention cover all modifications, equivalents, and alternatives falling within the spirit and scope of the invention as defined by the claims.

BRIEF DESCRIPTION OF THE DRAWINGS

The accompanying drawings, which are incorporated into and constitute a part of the specification, illustrate specific embodiments of the present invention and, together with the general description given above, and the detailed description of the specific embodiments, serve to explain the principles of the invention.

DETAILED DESCRIPTION OF THE INVENTION

Figure 1:
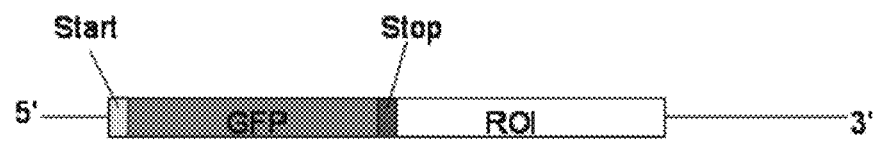
FIG. 1 is a diagrammatic representation of an mRNA molecule transcribed by one or more embodiments of a vector.

Referring to the drawings and the following detailed description, information about the present invention is provided including the description of specific embodiments, and the detailed description serves to explain the principles of the invention. The present invention is susceptible to modifications and alternative forms and is not limited to the particular forms disclosed. The present invention covers all modifications, equivalents, and alternatives falling within the spirit and scope of the invention as defined by the claims.

The present invention in part relates to a nucleic acid comprising the nucleic acid sequence of SEQ ID NO:1, and also relates to a plasmid comprising: a first signal protein sequence operably linked to a first promoter capable of controlling expression of the first signal protein in fungus; a second signal protein sequence operably linked to a second promoter capable of controlling expression of the second signal protein in fungus; and a cloning site for a gene of interest positioned in a 3-prime untranslated region of the first signal protein sequence; wherein when a gene of interest is inserted into the cloning site, the plasmid is capable of transcribing an mRNA that codes for both the first signal protein and the gene of interest. The plasmid can comprise the nucleic acid sequence of SEQ ID NO:1. The plasmid can further comprise a gene of interest inserted into the cloning site. The gene of interest can comprise a double-stranded RNA sequence capable of activating RNA-dependent Induced Silencing Complex (RISC). The present invention also relates to a transformed fungus comprising the plasmid of the present invention. The plasmid can be stably incorporated into the genome of the fungus. The present invention also relates to a vector comprising the nucleic acid of the present invention and to a method of transforming a fungus, wherein the plasmid is introduced into the fungus genome. Also, the present invention relates to a method of assessing the effects of RNA interference in a fungus, comprising: transforming the fungus of the present invention with the plasmid of the present invention; and detecting the presence or absence of one or more of the first signal protein and the second signal protein. One or more signal proteins can comprise green fluorescent protein, red fluorescent protein, yellow fluorescent protein, cyan fluorescent protein, orange fluorescent protein, or far-red fluorescent protein. The present invention also relates to an in vivo assay system for determining the effect of RNA interference on fungi comprising: a composition of fungi cells; the plasmid of the present invention; and an imaging device. In the in vivo assay system, the fungi can comprise *Cryptococcus*. The present invention further relates to a vector capable of transforming fungi. In one or more embodiments, the vector can comprise, for example, a plasmid such as pCryptoRNAi illustrated in FIG. 9, although the vector is not limited to a plasmid and can comprise a plasmid, a virus, a phage, an artificial chromosome, or the like.

Figure 9:
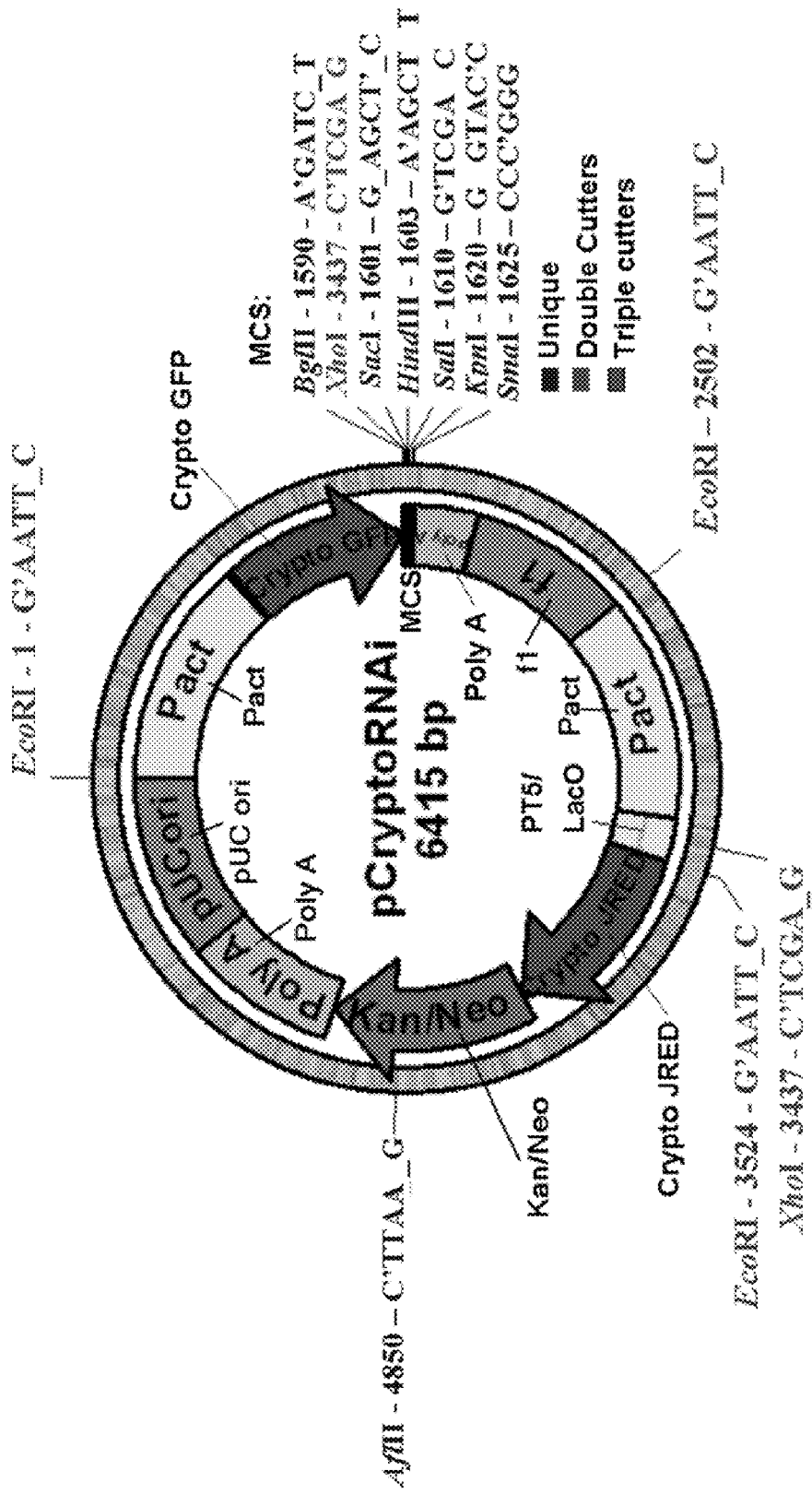
FIG. 9 is a diagrammatic representation of pCryptoRNAi plasmid according to one or more embodiments of the present invention.

Referring to FIG. 9, the plasmid can comprise a first signal protein sequence operably linked to a first promoter capable of controlling expression of the first signal protein in fungi. The first signal protein sequence can code for a signal protein such as, for example, green fluorescent protein, red fluorescent protein, yellow fluorescent protein, cyan fluorescent protein, orange fluorescent protein, or far-red fluorescent protein. The first signal protein sequence can be "cryptocosized", i.e., optimized for high expression in *Cryptococcus*, for example, having codon usage specific for *Cryptococcus neoformans*. As shown in FIG. 9, the cryptocosized signal protein can comprise green fluorescent protein (Crypto GFP). In some embodiments, the signal protein can comprise green fluorescent protein TurboGFP, which is a variant of the green fluorescent protein CopGFP cloned from copepod *Pontellina plumata* (Shagin et al., "GFP-like proteins as ubiquitous metazoan superfamily: evolution of functional features and structural complexity." Mol. Biol. Evol. 2004; 21(5):841-50).

In one or more embodiments, the first promoter can comprise, for example, a *Cryptococcus* actin promoter (Pact).

In one or more embodiments, the plasmid can further comprise a second signal protein sequence operably linked to a second promoter capable of controlling expression of the second signal protein in fungus. The second signal protein sequence can code for a signal protein such as, for example, green fluorescent protein, red fluorescent protein, yellow fluorescent protein, cyan fluorescent protein, orange fluorescent protein, or far-red fluorescent protein. The first signal protein and the second signal protein can be distinguishable from each other. As shown in FIG. 9, the second signal protein sequence can code for the red fluorescent protein JRED, which protein is obtained by mutagenesis of Anthomedusae jellyfish chromoprotein. (Shagin et al., "GFP-like proteins as ubiquitous metazoan superfamily: evolution of functional features and structural complexity." Mol. Biol. Evol. 2004; 21(5):841-50). In one or more embodiments, the second promoter can comprise, for example, a *Cryptococcus* actin promoter (Pact).

In one or more embodiments, the plasmid can further comprise a cloning site for a gene of interest. The cloning site can comprise a multiple cloning site (MCS), and can be positioned, for example, in the 3-prime untranslated region of the first signal protein sequence. In one or more embodiments, a GOI can be inserted into the cloning site, wherein, when a GOI is inserted into the cloning site, the plasmid can be capable of transcribing mRNA that codes for both the first signal protein and the GOI. A desired GOI of interest can comprise, for example, a PCR amplification product, and can be cloned using restriction enzymes into the cloning site. In one or more embodiments, the GOI can be tagged with a 5-prime signal protein, for example, green fluorescent protein (GFP).

Referring to FIG. 9, in one or more embodiments, the plasmid can further comprise an origin of replication (pUC ori) for propagation in *E. coli*, and an f1 origin (f1) for single-stranded DNA production. The plasmid can further comprise one or more gene conferring drug resistance, for example, kanamycin resistance (Kan$^r$) in *E. coli*, and/or neomycin resistance (Neo$^r$) in mammalian cells. To increase signal protein mRNA translation efficiency, the plasmid can comprise a Kozak consensus translation initiation site generated upstream of the first and/or second signal protein coding sequence.

In one or more embodiments of the present invention, a vector, for example a plasmid, can make a target RNA sequence visible using Crypto GFP. An mRNA coding gene sequence of a GOI can be inserted into the 3'-UTR of the Crypto GFP, which when transformed into a cell will produce a CryptoGFP mRNA having the 3'-UTR sequence of an RNA Of Interest (ROI), as shown in FIG. 1.

Figure 2:
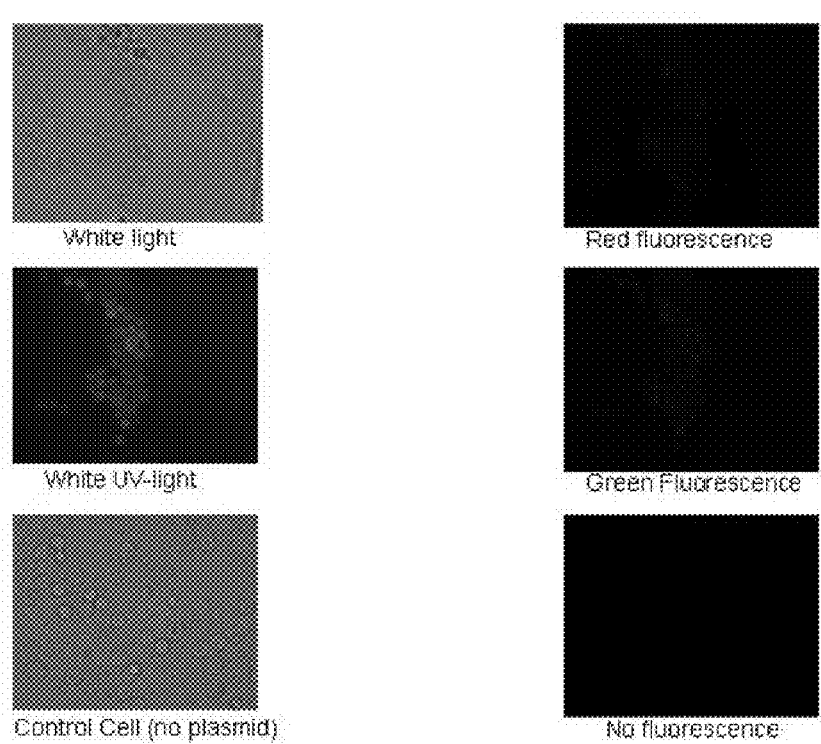
FIG. 2 is a set of photographs of *Cryptococcus* transformed with plasmids expressing green fluorescent protein and/or red fluorescent protein.

In one or more embodiments, the ROI can be silenced by using any technique that will cause the specific degradation of the ROI sequence (e.g., siRNA, dsRNA, inverted RNA, miRNA, and the like). In one or more embodiments, the entire GFP-ROI mRNA can be degraded causing the cell not to express GFP, and thus, no green fluorescence will be observed. FIG. 2 shows the illumination of GFP and/or JRED in *Cryptococcus* cells transformed with a vector according to one or more embodiments of the present invention, or with a control vector. Single colonies of *Cryptococcus neoformans* B4500 serotype D transformed with pCryptoRNAi were cultured in 15 ml YPG liquid media with 0.05 mg/ml G418 (an aminoglycoside Neomycin analogue for Kan/Neo resistance selection in eukaryotes) overnight. Ten (10)μl of fresh culture were diluted 1/200 in sterile distilled water and 10 μl of this dilution were used for UV microscopy. Cells were visualized for GFP and RFP fluorescence using an Olympus BX60 microscope with an Olympus BH2 RFL T3 burner, and photos taken with an Olympus DP11 digital camera system.

When transformed into *Cryptococcus* cells in the absence of a functional siRNA, according to one or more embodiments, a plasmid can express both JRED and GFP proteins. In this case, the brightness of GFP can significantly prevail. In the presence of siRNA directed against the cloned GOI, GFP expression and fluorescence, for example CryptoGFP, can be knocked down, while JRED expression can remain unchanged or (in some experimental systems) even increase due to translational competition. Thus, one or more embodiments of the vector can make it possible to trace RNA interference in the transformed fungi by turning off/on green fluorescence against a background of red fluorescence.

In one or more embodiments of the present invention, a vector can be used in RNAi-related applications, for example, to test the ability of synthetic siRNA oligonucleotides to knock down the expression of a GOI in fungi. In one or more embodiments, a gene of interest can be cloned into the vector, and the vector can be delivered into the fungi together with, for example, tested siRNA. In the embodiments exemplified in FIG. 9, the second signal protein (JRED) can function, for example, as a positive transformation marker, and the first signal protein (CryptoGFP) can function as an indicator of siRNA efficiency. Increasing red/green fluorescence intensity ratio compared to control experiments can indicate successful performance of siRNAs.

Figure 3:
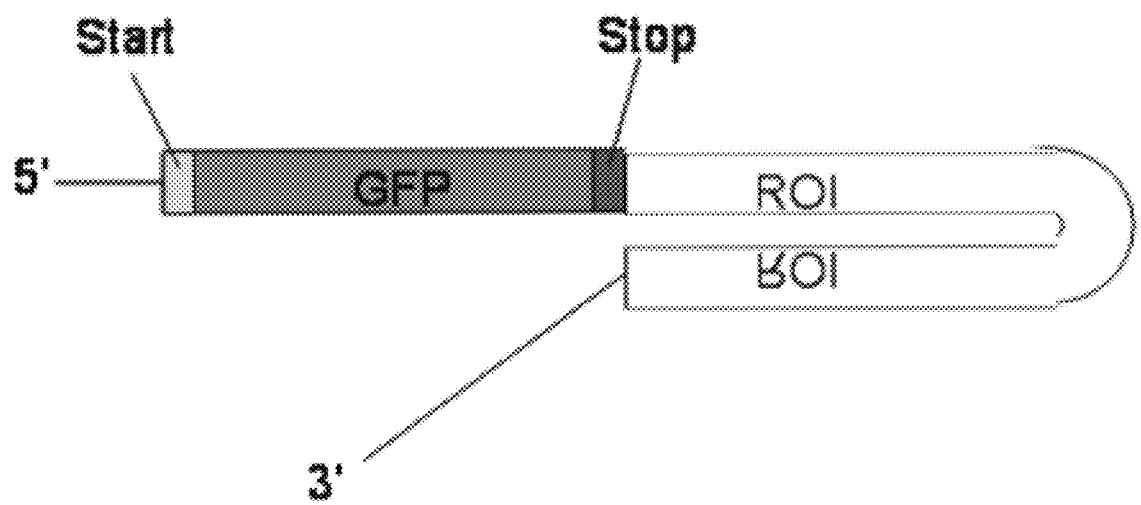
FIG. 3 is a diagrammatic representation of an mRNA molecule transcribed by one or more embodiments of a vector.

In one or more embodiments, the vector can provide GFP-tagged gene silencing. As shown in FIG. 3, a gene sequence corresponding to a GOI dsRNA sequence can be inserted into a cloning site of a vector. Accordingly, a structure shown in FIG. 3 can be transcribed into mRNA. This structure can produce dsRNA interference with the mRNA of the ROI sequence cloned. The dsRNA can activate RISC which can produce a degradation of the mRNA whose sequence is homologous to the ROI (i.e., endogenous ROI), and a degradation of the GFP tagged dsRNA. This can result in two phenotypes, that corresponding to the lacking homologous endogenous ROI sequence, and that corresponding to a lack of GFP fluorescence. In this way, RNA interference can be followed using GFP.

In one or more embodiments of the present invention, a fungus can be transformed with a vector, for example, pCryptoRNAi plasmid shown in FIG. 9. The fungus can be transformed by methods known to one of ordinary skill in the art, for example, reverse transfection, electroporation, biolistic transformation, viral infection and/or *Agrobacterium tumefaciens* mediated transformation. In some embodiments, the plasmid can be stably integrated into the genome of the fungus.

Construction of pCryptoRNAi Plasmid

The pCryptoRNAi plasmid comprising the nucleic acid sequence of SEQ ID NO:1 was prepared as follows. Plasmid p2FP-RNAi (Evrogen, Moscow, Russia) (SEQ ID NO:2) was cloned into *E. Coli* DH5α cells using the Electromax cloning kit (Invitrogen Corp., Carlsbad, Calif.) and transformed by electroporation according to the manufacturer's instructions. Bacterial colonies were propagated on 10 µl/ml kanamycin LB media overnight. Plasmid DNA isolation was done using the alkaline lysis method (Sambrook, Joseph, Russell, David W., "Protocol 2: Preparation of plasmid DNA by Alkaline Lysis with SDS: Minipreparation", Molecular Cloning: A laboratory Manual, Third edition, Cold Spring Harbor Laboratory Press, 2001, pages 1.35-1.37). Plasmid DNA was then digested with Bgl2 to produce a linear DNA molecule. The Bgl2 digested plasmid was electrophoresed on a 0.8% Agarose gel containing 0.02 µl/ml ethidium bromide and visualized under an UV-transilluminator. A correct 5.8 Kbp fragment could be seen.

The first CMV promoter ($P_{CMV\,IE}$) was substituted as follows. Three PCR reactions using 1 µl of linearized plasmid DNA as a template were set up. The first PCR product (alpha-A) was amplified using primer p13KAN0S01Afl2 (5'-GGCTTAAGGCGAGCATGCCCGA-3') (SEQ ID NO:3) and primer p5p2FP0A01 (5'-CGCAGCCTAAGGGCGAATTCTATCCACAGAATCAG GGGAT-3') (SEQ ID NO:4) to give a product of approximately 1589 base pairs. In this PCR reaction, a single nucleotide mutation was introduce to change a common restriction enzyme site (Sml1 at 4301 bp) into a unique Afl2 restriction site (shown in bold above). In this single nucleotide mutation, a cytosine (C) of the original plasmid kanamycin sequence was changed for a thymine (T), thus providing a unique restriction site without altering the amino acid sequence of the transcribed kanamycin resistance protein.

The Afl2 restriction site was introduced for the following reasons:
1. In order to substitute the two CMV promoters of p2FP-RNAi ($P_{CMVIE}$) by PCR fusion, the plasmid can be cut in half to prevent fused DNA fragments from misaligning by base complementation. As a result, the two CMV promoters can be substituted by, for example, two Pact promoters in independent reactions without their homologous sequences interfering with each other.
2. To disrupt the KAN gene so that only ligated fragments with the correct DNA sequence will reconstruct the KAN/NEO resistance gene and produce a resistant phenotype that can be selected with Kanamycin (in *E. coli*) and G418 (in *Cryptococcus*)

Because the entire KAN sequence lacked a unique restriction site, there was a need for introducing a restriction site that would not alter the Kan protein function. By changing a single nucleotide (CTG→CTT) the amino acid codon can remain the same (Leu), but the restriction site can be changed to Afl2 which is unique in the plasmid sequence.

The *Cryptococcus* actin promoter was amplified from Strain B4500 serotype D genomic DNA. B4500 serotype D mating type a stain is available in the laboratory of Dr. Yamaguchi, Department of Molecular Function, Medical Mycology Research Center, Chiba University, Japan. Extraction of the B4500 DNA was done using the glass bead miniprep procedure with some modifications (Sambrook, Joseph, Russell, David W., "Rapid Isolation of Yeast DNA", Molecular Cloning: A Laboratory Manual, Third edition, Cold Spring Harbor Laboratory Press, 2001, page 6.31-6.32). More specifically, the DNA extraction was performed as follows: (1) add one loop of cells to 150 µl DTAB (dodecyltrimethylammonium bromide) lysis solution (8% DTAB, 1.5M NaCl, 100 mM Tris-Cl (pH 8.0), 50 mM EDTA) containing 0.1 µl DNase-free RNase in 2 ml screw-cap tubes with acid washed glass beads (Sigma-Aldrich, St. Louis, Mo.), (2) process in FastPrep® FP100A cell disrupter (Bio101, Inc., La Jolla, Calif.) at speed 4.5 for 30 seconds, twice, (3) incubate at 68° C. for 20 min, (4) add 250 µl chloroform, mix, (5) centrifuge 13000 rpm, 10 min, (6) transfer supernatant (100 µl) to 1.5 µl microfuge tube (pre added with 300 µl dH$_2$O and 50 µl CTAB (cetyltrimethylammonium bromide; 5% CTAB, 0.4M NaCl) and mix, (7) centrifuge 13000 rpm, 5 min, (8) discard supernatant and dissolve pellet in 80 µl 1.2M NaCl, (9) add 500 µl ice cold 100% ethanol, (10) centrifuge at 13000 rpm, 4° C. for 15 min, (11) discard supernatant, (12) add 250 µl 70% Ethanol, mix, (13) centrifuge at 13000 rpm, 4° C. for 10 min, (14) discard supernatant, (15) dry pellets at room temperature for 15 min, (16) add 50 μl TE (10 mM Tris-Cl pH 7.5, 1 mM EDTA) buffer.

The amplification of the *Cryptococcus* actin promoter was done using fusion primer p1Pact0S02 (5'-ATCCCCTGAT-TCTGTGGATAGAATTCGCCCTTAGGCTGCG-3') (SEQ ID NO:5) and primer p2PactOA02 (5'-GGCGACCGG-TAGCGCTAGCGGTGGCGGCCGCCATAGACAT-3') (SEQ ID NO:6) producing a 900 base pair amplification product (alpha-B). The sequence corresponding to the actin promoter is shown underlined.

For the third PCR reaction, a reaction was set up using primer p6p2FP0S01 (5'-ATGTCTATGGCGGCCGCCAC CGCTAGCGCTACCGGTCGCC-3') (SEQ ID NO:7) and primer p4Bgl20A01 (5'-GGGAGATCTTCCGGGATCAT-TCT-3') (SEQ ID NO:8), producing a fragment of 757 base pairs (alpha-C).

Figure 4:
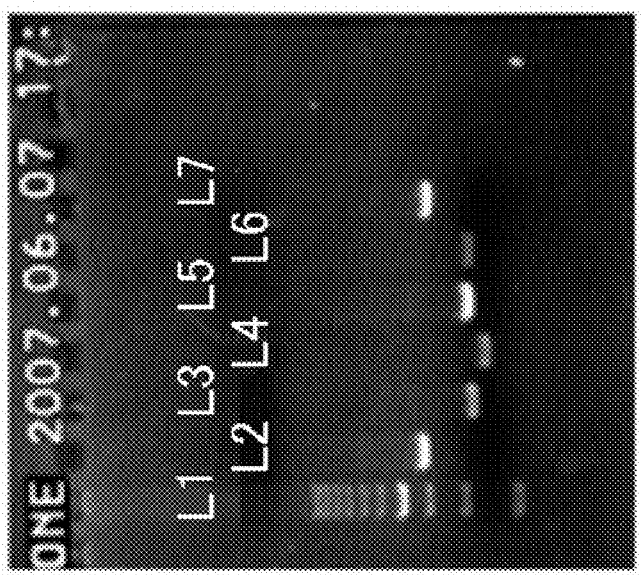
FIG. 4 is a photograph of agarose gel electrophoresis of PCR amplification products used to construct one or more embodiments of a plasmid.

All first round fusion amplification reactions were done using KODplus polymerase (Toyobo Biologics, Inc., Osaka, Japan) with PCR cycles of 94° C. for 4 minutes for 1 cycle, 94° C. for 1 minute, 55° C. for 1 minute and 72° C. for 5 minutes for 30 cycles, and a final elongation step at 72° C. for 7 minutes. The first round fusion amplification products (alpha-A, alpha-B, and alpha-C) were confirmed by agarose-gel electrophoresis (FIG. 4).

Figure 5:
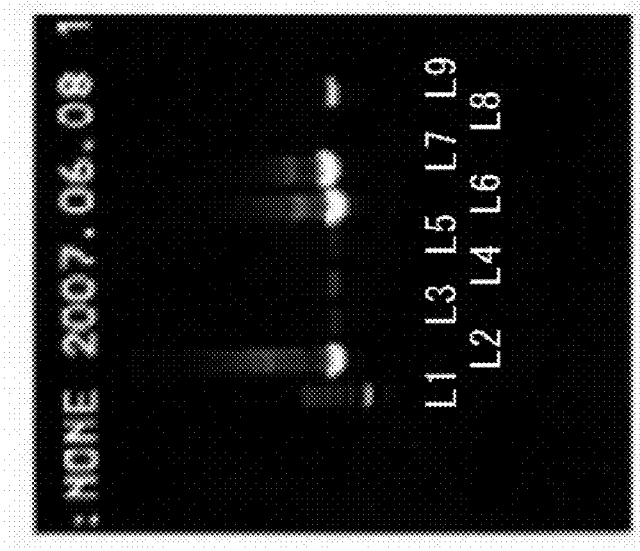
FIG. 5 is a photograph of agarose gel electrophoresis of PCR amplification products used to construct one or more embodiments of a plasmid.

The amplification products (alpha-A, alpha-B and alpha-C) were gel purified using QIAquick gel extraction kit (Qiagen, Inc., Valencia, Calif.). One μl of each gel purified amplification product was combined together in a second round fusion PCR reaction using primer p13KAN0S01Afl2 and primer p4Bgl20A01 to produce a fusion PCR amplification product (2alpha) of 3206 base pairs. The second round fusion amplification products were confirmed by agarose-gel electrophoresis (FIG. 5).

Similarly, three PCR reactions were performed to substitute the second CMV promoter region ($P_{CMV IE}$) downstream of the multiple cloning site (MCS) in p2FP-RNAi by fusion PCR amplification using one (1) μl of linearized plasmid as a template. In this case, the first PCR reaction was done using primer p3Bgl20S01 (5'-GGGAGATCTCGAGCT-CAAGCTTC-3') (SEQ ID NO:9) and primer p9P2FP0A01 (5'-CGCAGCCTAAGGGCGAATTCCTAACTGACACAC ATTCCAC-3') (SEQ ID NO:10), yielding a 915 base pair product (beta-1). The underlined region of primer p9PFP0A01 corresponds to the 5' region of the actin promoter.

The actin promoter was PCR amplified in a second PCR reaction using primer p7 Pact0S01 (5'-GTGGAATGTGTGT-CAGTTAGGAATTCGCCCTTAGGCTGCG-3') (SEQ ID NO:11) and primer p8Pact0A01 (5'-ATAATGGTTTCTTAC-TAGCGGTGGCGGCCGCCATAGACAT-3') (SEQ ID NO:12), producing a 900 base pair product (beta-2).

For the third fusion PCR reaction, primer p10RFP0S01 (5'-ATGTCTATGGCGGCCGCCACCGCTAGTAAGAAACC ATTAT-3') (SEQ ID NO:13) and primer p14KAN0A01Afl2 (5'-TCGGGCATGCTGGCCTTAAGCC-3') (SEQ ID NO:14) were used, yielding a 1516 base pair product (beta-3).

The amplification products (beta-1, beta-2 and beta-3) were confirmed by agarose-gel electrophoresis (FIG. 4). Primer p14KAN0A01Afl2 had the complementary mutation in the Kan$^r$/Neo$^r$ open reading frame (ORF) to change the Sml1 restriction site to an Afl2 unique restriction site without affecting the amino acid sequence of the transcribed protein.

For the second round PCR fusion reaction, 1 μl of each amplification product (beta-1, beta-2 and beta-3) was used as template and amplification was done using primer p3Bgl20S01 and primer p14KAN0A01Afl2. This PCR fusion reaction was performed at 94° C. for 1 minute, 94° C. for 1 minute, 60° C. for 1 minute, 72° C. for 5 minutes for 30 PCR cycles, and a final extension of 7 minutes at 72° C. The fusion PCR amplification reaction produced a 3291 base pair product (2beta).

Figure 6:
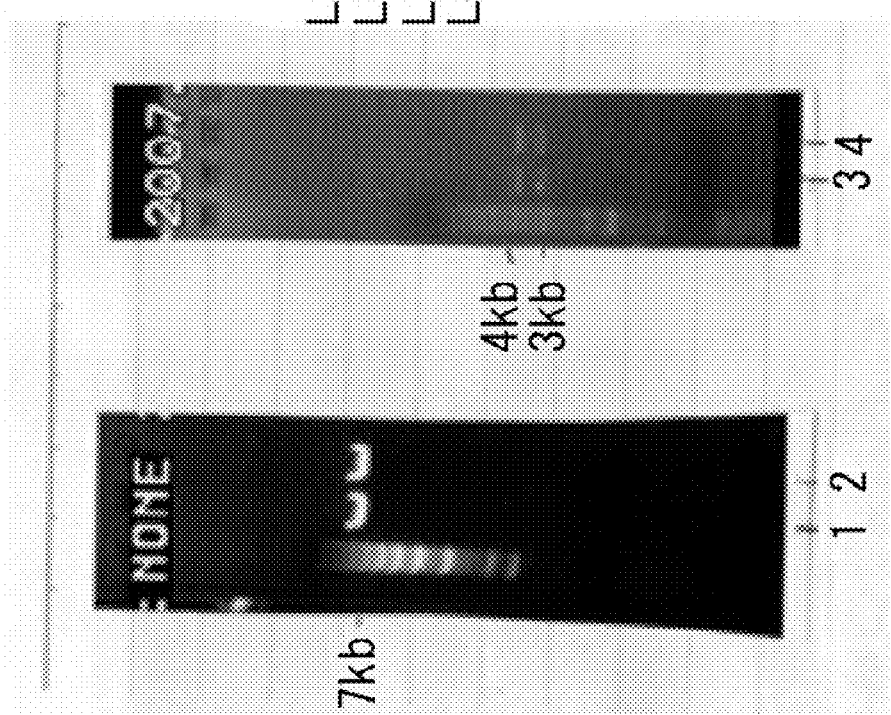
FIG. 6 is a photograph of agarose gel electrophoresis of restriction enzyme digested plasmid DNA used to construct one or more embodiments of a plasmid.

The second Round Fusion amplification products were confirmed by agarose-gel electrophoresis (FIG. 5). All PCR reactions were performed using KODplus polymerase enzyme (Toyobo Biologics, Inc., Osaka, Japan). 2Alpha and 2beta were gel purified using QIAquick gel purification kit (Qiagen, Inc., Valencia, Calif.) and 2 μl of each purified DNA was used in separate reactions for cloning into Topo4blunt-PCR cloning vector (Invitrogen Corp., Carlsbad, Calif.) using the Topo4-blunt-PCR cloning kit (Invitrogen Corp., Carlsbad, Calif.) following the manufacturer's recommendations. Transformed *E. coli* DH5α cells were screened on kanamycin containing LB media for 2 to 3 days at 37° C. Candidate colonies were inoculated in liquid LB medium containing 5 μl/ml kanamycin in separate tubes and incubated overnight at 37° C. Plasmid isolation was done using the alkaline lysis method by standard protocol. The resultant DNA extracted from 2 colonies (2b1, and 2a3) was digested with Bgl2 to give an expected product of approximately 7000 base pairs (FIG. 6, lanes 1 and 2). The Bgl2 digestion products were further digested with Afl2, resulting in two expected products of approximately 4000 base pairs and approximately 3000 base pairs (FIG. 6, lanes 3 and 4).

To further analyze the correct sequence of the cloned fused fragment and the single nucleotide mutation introduced by PCR amplification, the cloned DNA was sequenced using primers T3 5'-GCAATTAACCCTCACTAAAG-3' (SEQ ID NO:15) and T7 5'-TAATACGACTCACTATAGGG-3' (SEQ ID NO:16) and provided with the TOPO4blunt-PCR cloning kit as standard protocol. Samples were sequenced using an ABI3100 sequencer (Applied Bioscience, Foster City, Calif.) and analyzed with the software provided. The sequencing data revealed the correct sequence of the cloned fragments, and in particular of the single nucleotide mutation in the Kan$^r$/Neo$^r$ ORF.

Each Topo4 vector-cloned fragment was digested with Bgl2 after which the digestion product was column purified using QIAquick PCR nucleotide removal kit (Qiagen, Inc., Valencia, Calif.) to change buffer, and then digested again with Afl2. Double digested DNA was run on a 0.8% agarose gel where one 4 kbp and one 3 kbp bands were seen. The 3 kbp bands corresponding to the excised fused fragments (2alpha and 2beta) were gel purified using QIAquick gel extraction kit (Qiagen, Inc., Valencia, Calif.) and concentrated under rotary evaporation.

Figure 7:
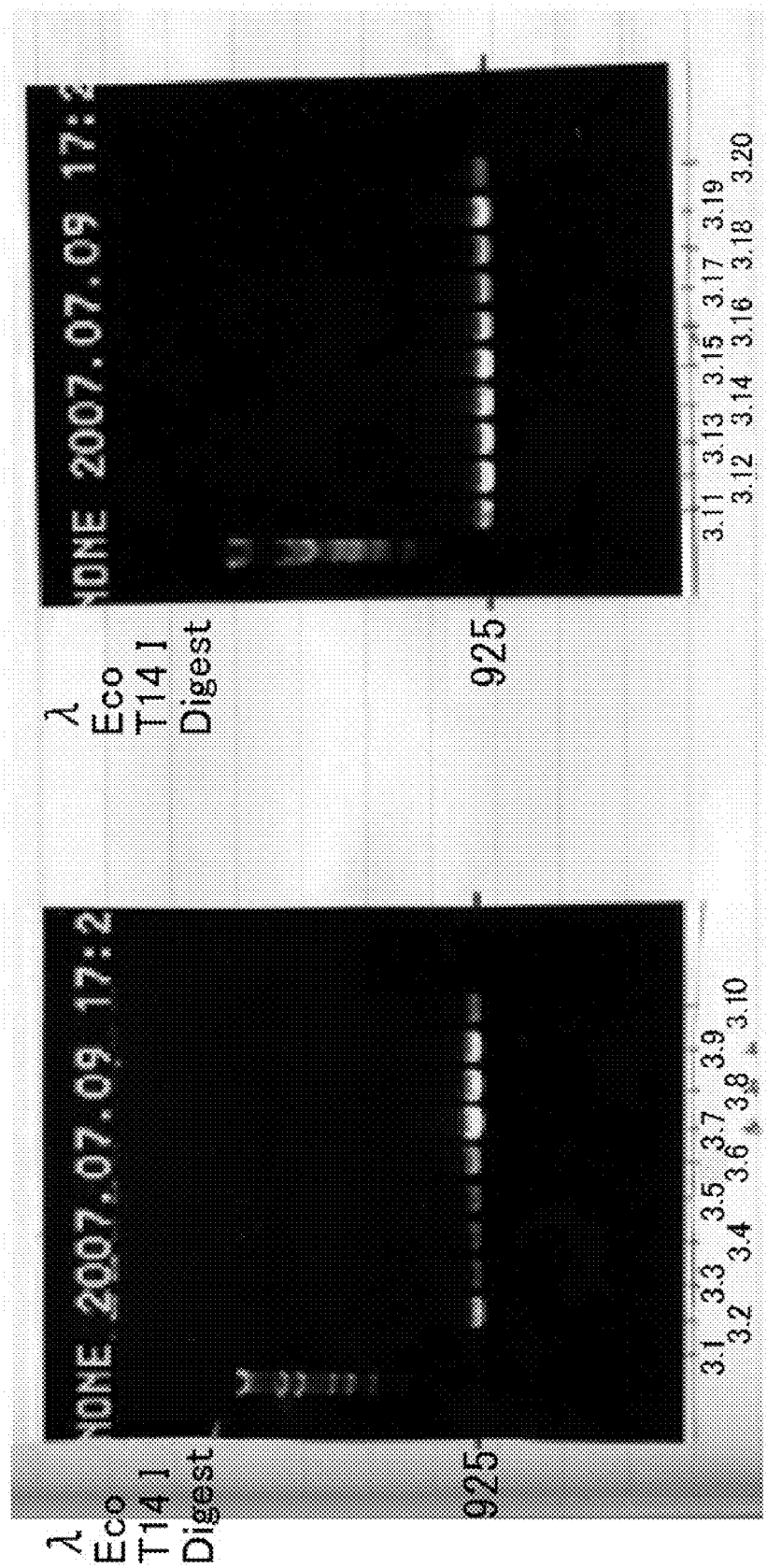
FIG. 7 is a photograph of agarose gel electrophoresis of PCR amplification products used to construct one or more embodiments of a plasmid.
Figure 8:
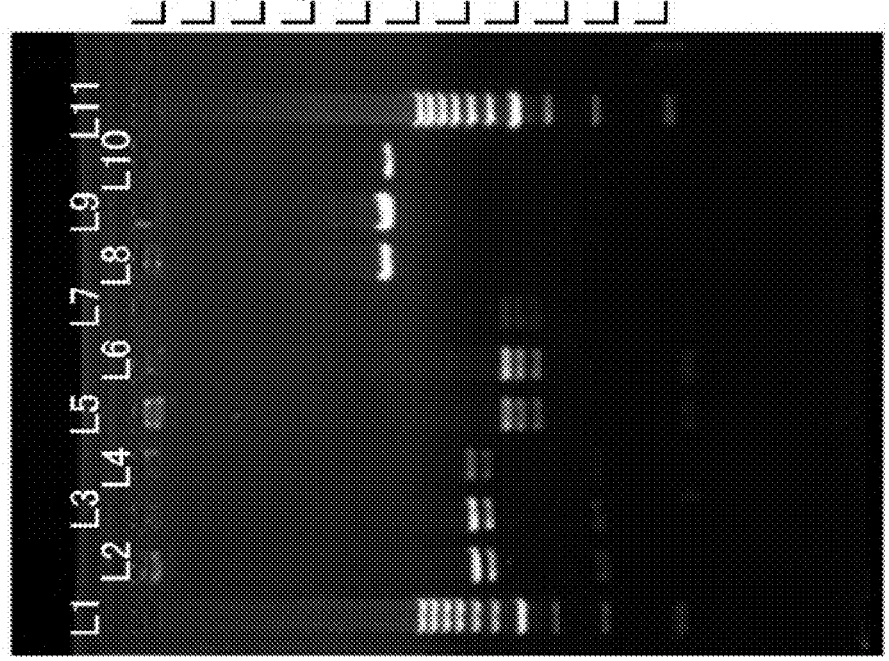
FIG. 8 is a photograph of agarose gel electrophoresis of restriction enzyme digested pCryptoRNAi plasmid DNA according to one or more embodiments of the present invention.

Fragment 2alpha and fragment 2beta were ligated overnight using T4 DNA ligase at 4° C. for 36 hours. The ligation reaction was then passed through a Sephadex-G50 column for desalting. One μl of desalted ligation product was used for cloning into *E. coli* DH5α cells as standard protocol. Transformants were cultured on 10 μg/ml kanamycin LB plates for positive selection at 37° C. for a couple of days. Transformant colonies were screened by colony PCR using p1Pact0S02 and p2PactOA02 showing a 900 bp amplification product. Specifically, *E. coli* DHα transformants were screened for *Cryptococcus* actin promoter (925 bp) by colony PCR using primers p1Pact0S02 and p2PactOA02. Colonies 3.7, 3.8, 3.9, and 3.12 (see, FIG. 7) were selected for plasmid DNA extraction using the alkaline lysis method. The plasmids were extracted using the alkaline lysis protocol and digested with Hind3 following the manufacturer's recommendation to give the expected 6.2 kbp digestion product. Extracted plasmid DNA numbers 3.8, 3.9 and 3.12 were further digested using exonuclease enzymes EcoRI (giving expected fragments of 2900, 2506 and 1028 base pairs), SphI (giving expected fragments of 2109, 1893, 1500 and 411 base pairs) and Afl2 (giving an unique expected product of 6415 base pairs). The digestion profile of the completed pCryptoRNAi plasmid constructs is shown in FIG. 8.

Effect of the pCryptoRNAi Plasmid Vector

Figure 10:
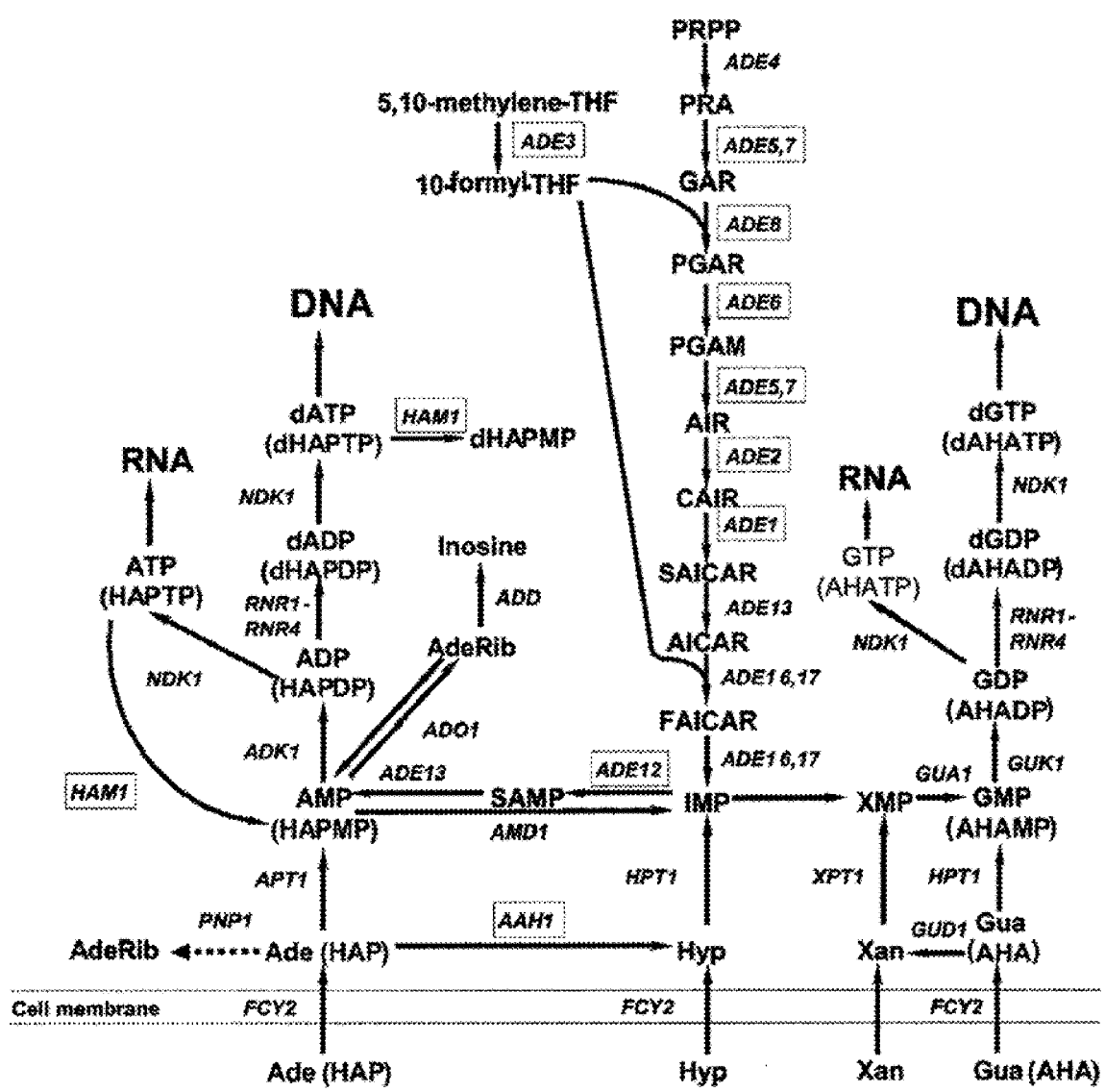
FIG. 10 is a diagram illustrating purine salvage and purine biosynthesis de novo pathways in yeast (Stepchenkova et al., BMC Genetics, 2005, 6:31).

The pCryptoRNAi plasmid vector was tested for the effect as a molecular tool for the study of RNAi in *Cryptococcus*, using a construct coding for *Cryptococcus neoformans* phosphoribosyl aminoimidazole carboxylase (ADE2) gene cloned into the pCrypto-RNAi plasmid as a ROI palindrome sequence (i.e., as exemplified and illustrated in FIG. 3). ADE2 gene expression can be monitored by a visual color assay, and with reference to FIG. 10. Pink cells due to the accumulation of phosphoribosyl aminoimidazole were observed.

After activation of RISC by the ADE2 ROI palindrome mRNA, the pCryptoRNAi ADE2 dsRNA is cleaved producing endogenous siRNA, which interferes with the endogenous ADE2 mRNA, producing a silencing of the ADE2 gene. In this situation, mRNA levels corresponding to the phosphoribosyl aminoimidazole carboxylase enzyme (ADE2) decrease, and phosphoribosyl aminoimidazole (AIR) accumulates in the cell making the cell pink. Colonies resulting in a pink color indicate the correct expression of the pCryptoRNAi ADE2 palindrome dsRNA and the functional silencing of the endogenous ADE2 gene.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

What is claimed is:

1. A nucleic acid comprising the nucleic acid SEQ ID NO: 1.

2. A vector comprising the nucleic acid of claim 1.

3. The vector of claim 2, wherein the vector is a plasmid vector.

4. The vector of claim 3, further comprising a gene of interest inserted into a cloning site in the vector.

5. The vector of claim 4, wherein the gene of interest comprises a double-stranded RNA sequence capable of activating RNA-dependent Induced Silencing Complex (RISC).

6. A transformed fungus comprising the vector of claim 3.

7. The transformed fungus of claim 6, wherein the vector is stably incorporated into the genome of the fungus.

8. A method of transforming a fungus, wherein the vector of claim 3 is introduced into the fungus genome.

9. A method of assessing the effects of RNA interference in a fungus, comprising:
   transforming the fungus with a plasmid vector comprising SEQ ID NO: 1 and a gene of interest inserted into a cloning site in the plasmid vector; and
   detecting the presence or absence of one or more of a first signal protein and a second signal protein encoded by the plasmid vector.

10. An in vivo assay system for determining the effect of RNA interference on fungi comprising:
    a composition of fungi cells;
    the vector of claim 4; and
    an imaging device.

11. The in vivo assay system of claim 10, wherein the fungi comprise *Cryptococcus*.

* * * * *

```
                          SEQUENCE LISTING

<160> NUMBER OF SEQ ID NOS: 16

<210> SEQ ID NO 1
<211> LENGTH: 6415
<212> TYPE: DNA
<213> ORGANISM: Artificial
<220> FEATURE:
<223> OTHER INFORMATION: Designed polynucleotide based on plasmid DNA,
      which is named pCryptoRNAi

<400> SEQUENCE: 1
gaattcgccc ttaggctgcg ggaggtgagc tggagagcgg cgcacgggaa ggggaggact    60
cacataagca tgcaggattc gagtggcatg gtgtgcactg agtgtatggt tgtcggagga   120
gaggatgatg gtaacaacaa tagcagcaac gtcactcgac gcgcgtccgg tgtgccacac   180
ggggtaacgc cgagtcgccg tcagggtcgc cgagaccact ctcacagcgt caccgttggc   240
accagctcag cttacagctt ctatcctccg ccagcatcca catacatccc ctataccgca   300
tcccccaccc actgcccaag gtgagtcatc ttcccgcccc cttcccttgc ccgccactca   360
gtcctccatc ctccactaat ccaccttatc gcacccaccg cctatcgcac atccgagcac   420
aatgctgggc ctgccagggg ctgctagatg gtgctctccc cacgctgatc tgcatgccgg   480
ccattggatc atgggtgcta ggtgctgggt gctggatgtt ggatgctgga tgctgggtgc   540
acgcttggtc atttccttcc aggattgacg gtcgccgaga ggacgacgtg gcgttcgaca   600
acgagggccg atagcaccgc atcgcctcga cctgcatcca tctcgccttg tccttttggt   660
gcaacaatcc atccgtgctg gtgccacacg catagctgga agagatggat gtgcgttgaa   720
cagagctgcc gtcaggactt tttggtgcac ggaccctatt gtcctcccca atcttcaccg   780
cgtctcctaa tatgcagcct ctttgctaat tgtcttttc cattagtaaa ctcgcccaac   840
atgtctatgg cggccgccac cgctagcgct accggtcgcc accatggaga gcgacgagag   900
cggcctgccc gccatggaga tcgagtgccg catcaccggc accctgaacg gcgtggagtt   960
cgagctggtg ggcggcggag agggcacccc cgagcagggc cgcatgacca acaagatgaa  1020
```

```
gagcaccaaa ggcgccctga ccttcagccc ctacctgctg agccacgtga tgggctacgg    1080
cttctaccac ttcggcacct accccagcgg ctacgagaac cccttcctgc acgccatcaa    1140
caacggcggc tacaccaaca cccgcatcga aagtacgag gacggcggcg tgctgcacgt     1200
gagcttcagc taccgctacg aggccggccg cgtgatcggc gacttcaagg tgatgggcac    1260
cggcttcccc gaggacagcg tgatcttcac cgacaagatc atccgcagca acgccaccgt    1320
ggagcacctg caccccatgg gcgataacga tctggatggc agcttcaccc gcaccttcag    1380
cctgcgcgac ggcggctact acagctccgt ggtggacagc cacatgcact tcaagagcgc    1440
catccacccc agcatcctgc agaacggggg ccccatgttc gccttccgcc gcgtggagga    1500
ggatcacagc aacaccgagc tgggcatcgt ggagtaccag cacgccttca agaccccgga    1560
tgcagatgcc ggtgaagaat gatcccggaa gatctcgagc tcaagcttcg tcgacggtac    1620
cgcccgggac tctagctaga tcataatcag ccataccaca tttgtagagg ttttacttgc    1680
tttaaaaaac ctcccacacc tccccctgaa cctgaaacat aaaatgaatg caattgttgt    1740
tgttaacttg tttattgcag cttataatgg ttacaaataa agcaatagca tcacaaattt    1800
cacaaataaa gcattttttt cactgcattc tagttgtggt ttgtccaaac tcatcaatgt    1860
atcttaacgc gtaaattgta agcgttaata ttttgttaaa attcgcgtta aattttgtt     1920 aaatcagctc attttttaac caataggccg aaatcggcaa aatcccttat aaatcaaaag    1980
aatagaccga datagggttg agtgttgttc cagtttggaa caagagtcca ctattaaaga    2040
acgtggactc caacgtcaaa gggcgaaaaa ccgtctatca gggcgatggc ccactacgtg    2100
aaccatcacc ctaatcaagt tttttggggt cgaggtgccg taaagcacta atcggaacc     2160 ctaaagggag cccccgattt agagcttgac ggggaaagcc ggcgaacgtg gcgagaaagg    2220
aagggaagaa agcgaaagga gcgggcgcta gggcgctggc aagtgtagcg gtcacgctgc    2280
gcgtaaccac cacacccgcc gcgcttaatg cgccgctaca gggcgcgtca ggtggcactt    2340
ttcggggaaa tgtgcgcgga accctatttt gttatttttt ctaaatacat tcaaatatgt    2400
atccgctcat gagacaataa ccctgataaa tgcttcaata atattgaaaa aggaagagtc    2460
ctgaggcgga aagaaccagc tgtggaatgt gtgtcagtta ggaattcgcc ttaggctgc     2520 gggaggtgag ctggagagcg gcgcacggga aggggaggac tcacataagc atgcaggatt    2580
cgagtggcat ggtgtgcact gagtgtatgg ttgtcggagg agaggatgat ggtaacaaca    2640
atagcagcaa cgtcactcga cgcgcgtccg gtgtgccaca cggggtaacg ccgagtcgcc    2700
gtcagggtcg ccgagaccac tctcacagcg tcaccgttgg caccagctca gcttacagct    2760
tctatcctcc gccagcatcc acatacatcc cctataccgc atcccccacc cactgcccaa    2820
ggtgagtcat cttcccgccc ccttcccttg cccgccactc agtcctccat cctccactaa    2880
tccaccttat cgcacccacc gcctatcgca catccgagca caatgctggg cctgccaggg    2940
gctgctagat ggtgctctcc ccacgctgat ctgcatgccg ccattggat catgggtgct     3000 aggtgctggg tgctggatgt tggatgctgg atgctgggtg cacgcttggt catttccttc    3060
caggattgac ggtcgccgag aggacgacgt ggcgttcgac aacgagggcc gatagcaccg    3120
catcgcctcg acctgcatcc atctcgcctt gtccttttgg tgcaacaatc catccgtgct    3180
ggtgccacac gcatagctgg aagagatgga tgtgcgttga acagagctgc cgtcaggact    3240
ttttggtgca cggaccctat tgtcctcccc aatcttcacc gcgtctccta atatgcagcc    3300
tctttgctaa ttgtcttttt ccattagtaa actcgcccaa catgtctatg gcggccgcca    3360
ccgctagtaa gaaaccatta ttatcatgac attaacctat aaaaataggc gtatcacgag    3420
```

-continued

```
gcccttcgt cttcacctcg agaaatcata aaaaatttat ttgctttgtg agcggataac      3480
aattataata gattcaattg tgagcggata acaatttcac acagaattca ttaaagagga      3540
gaaattaact atgagaggat cgcatcacca tcaccatcac ggatccgacg aggatggttc      3600
agagggcggc cccgccctgt tccagagcga catgaccttc aaaatcttca tcgacggcga      3660
ggtgaacggc cagaagttca ccatcgtggc cgacggcagc agcaagttcc cccacgcga       3720
cttcaacgtg cacgccgtgt gcgagaccgg caagctgccc atgagctgga agcccatctg      3780
ccacctgatc cagtacggcg agcccttctt cgcccgctac cccaacggca tcagccactt      3840
cgcccaggag tgcttccccg agggcctgag catcgaccgc accgtgcgct cgagaacga       3900
cggcaccatg accagccacc acacctacga gctggacggc acctgcgtgg tcagccgcat      3960
caccgtgaac tgcgacggct ccagcccga cggccccatc atgcgcgacc agctggtgga       4020
catcctgccc aacgagaccc acatgttccc ccacggcccc aacgccgtgc gccagctggc      4080
cttcatcggc ttcaccaccg ccgacggcgg cctgatgatg ggccacttcg acagcaagat      4140
gaccttcaac ggcagccgcg ccatcaagat ccccggcccc cacttcgtga ccatcatcac      4200
caagcagatg agggacacca gcgacaagcg cgaccacgtg tgccagcgcg aggtgaccta      4260
cgcccacagc gtgccccgca tcaccagcgc catcggtagc gacgaggatg gatctcgggt      4320
agatatctcg gccattgaac aagatggatt gcacgcaggt tctccggccg cttgggtgga     4380
gaggctattc ggctatgact gggcacaaca gacaatcggc tgctctgatg ccgccgtgtt      4440
ccggctgtca gcgcagggc gcccggttct ttttgtcaag accgacctgt ccggtgccct       4500
gaatgaactg caagacgagg cagcgcggct atcgtggctg gccacgacgg gcgttccttg      4560
cgcagctgtg ctcgacgttg tcactgaagc gggaagggac tggctgctat gggcgaagt      4620
gccggggcag gatctcctgt catctcacct tgctcctgcc gagaaagtat ccatcatggc     4680
tgatgcaatg cggcggctgc atacgcttga tccggctacc tgcccattcg accaccaagc     4740
gaaacatcgc atcgagcgag cacgtactcg gatggaagcc ggtcttgtcg atcaggatga     4800
tctggacgaa gagcatcagg ggctcgcgcc agccgaactg ttcgccaggc ttaaggcgag     4860
catgcccgac ggcgaggatc tcgtcgtgac ccatggcgat gcctgcttgc cgaatatcat     4920
ggtggaaaat ggccgctttt ctggattcat cgactgtggc cggctgggtg tggcggaccg     4980
ctatcaggac atagcgttgg ctacccgtga tattgctgaa gagcttggcg gcgaatgggc     5040
tgaccgcttc ctcgtgcttt acggtatcgc cgctcccgat tcgcagcgca tcgccttcta     5100
tcgccttctt gacgagttct tctgagcggg actctggggt tcgaaatgac cgaccaagcg     5160
acgcccaacc tgccatcacg agatttcgat tccaccgccg ccttctatga aaggttgggc     5220
ttcggaatcg ttttccggga cgccggctgg atgatcctcc agcgcgggga tctcatgctg     5280
gagttcttcg cccacccctag ggggaggcta actgaaacac ggaaggagac aataccggaa    5340
ggaacccgcg ctatgacggc aataaaaaga cagaataaaa cgcacggtgt tgggtcgttt     5400
gttcataaac gcggggttcg gtcccagggc tggcactctg tcgataccc accgagaccc      5460
cattgggcc aatacgcccg cgtttcttcc ttttccccac cccacccccc aagttcgggt      5520
gaaggcccag ggctcgcagc caacgtcggg gcggcaggcc ctgccatagc ctcaggttac     5580
tcatatatac tttagattga tttaaaactt cattttaatt ttaaaggat ctaggtgaag     5640
atccttttg ataatctcat gaccaaaatc ccttaacgtg agttttcgtt ccactgagcg     5700
tcagaccccg tagaaaagat caaaggatct tcttgagatc cttttttct gcgcgtaatc     5760
tgctgcttgc aaacaaaaaa accaccgcta ccagcggtgg tttgtttgcc ggatcaagag     5820
```

```
ctaccaactc tttttccgaa ggtaactggc ttcagcagag cgcagatacc aaatactgtc   5880
cttctagtgt agccgtagtt aggccaccac ttcaagaact ctgtagcacc gcctacatac   5940
ctcgctctgc taatcctgtt accagtggct gctgccagtg gcgataagtc gtgtcttacc   6000
gggttggact caagacgata gttaccggat aaggcgcagc ggtcgggctg aacggggggt   6060
tcgtgcacac agcccagctt ggagcgaacg acctacaccg aactgagata cctacagcgt   6120
gagctatgag aaagcgccac gcttcccgaa gggagaaagg cggacaggta tccggtaagc   6180
ggcagggtcg gaacaggaga gcgcacgagg gagcttccag ggggaaacgc ctggtatctt   6240
tatagtcctg tcgggtttcg ccacctctga cttgagcgtc gatttttgtg atgctcgtca   6300
ggggggcgga gcctatggaa aaacgccagc aacgcggcct ttttacggtt cctggccttt   6360
tgctggcctt tgctcacat gttctttcct gcgttatccc ctgattctgt ggata          6415
```

<210> SEQ ID NO 2
<211> LENGTH: 5886
<212> TYPE: DNA
<213> ORGANISM: Artificial
<220> FEATURE:
<223> OTHER INFORMATION: Designed Polynucleotide based on plasmid DNA,
      which is named Plasmid p2FP-RNAi

<400> SEQUENCE: 2

```
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagatcc gctagcgcta    600
ccggtcgcca ccatggagag cgacgagagc ggcctgcccg ccatggagat cgagtgccgc    660
atcaccggca ccctgaacgg cgtggagttc gagctggtgg cggcggaga gggcacccc    720 gagcagggcc gcatgaccaa caagatgaag agcaccaaag gcgccctgac cttcagcccc    780
tacctgctga gccacgtgat gggctacggc ttctaccact tcggcaccta cccagcggc    840 tacgagaacc ccttcctgca cgccatcaac aacggcggct acaccaacac ccgcatcgag    900
aagtacgagg acggcggcgt gctgcacgtg agcttcagct accgctacga ggccggccgc    960
gtgatcggcg acttcaaggt gatgggcacc ggcttccccg aggacagcgt gatcttcacc   1020
gacaagatca tccgcagcaa cgccaccgtg gagcacctgc accccatggg cgataacgat   1080
ctggatggca gcttcacccg caccttcagc ctgcgcgacg gcggctacta cagctccgtg   1140
gtggacagcc acatgcactt caagagcgcc atccacccca gcatcctgca gaacggggc   1200 cccatgttcg ccttccgccg cgtggaggag atcacagca acaccgagct gggcatcgtg   1260
gagtaccagc acgccttcaa gaccccggat gcagatgccg gtgaagaatg atcccggaag   1320
atctcgagct caagcttcgt cgacggtacc gcccgggact ctagctagat cataatcagc   1380
cataccacat ttgtagaggt tttacttgct ttaaaaaacc tcccacacct ccccctgaac   1440
```

-continued

```
ctgaaacata aaatgaatgc aattgttgtt gttaacttgt ttattgcagc ttataatggt      1500
tacaaataaa gcaatagcat cacaaatttc acaaataaag cattttttc actgcattct       1560 agttgtggtt tgtccaaact catcaatgta tcttaacgcg taaattgtaa gcgttaatat      1620
tttgttaaaa ttcgcgttaa attttttgtta aatcagctca ttttttaacc aataggccga    1680
aatcggcaaa atcccttata aatcaaaaga atagaccgag atagggttga gtgttgttcc     1740
agtttggaac aagagtccac tattaaagaa cgtggactcc aacgtcaaag ggcgaaaaac     1800
cgtctatcag ggcgatggcc cactacgtga accatcaccc taatcaagtt ttttggggtc     1860
gaggtgccgt aaagcactaa atcggaaccc taaagggagc ccccgattta gagcttgacg     1920
gggaaagccg gcgaacgtgg cgagaaagga agggaagaaa gcgaaggag cgggcgctag      1980 ggcgctggca agtgtagcgg tcacgctgcg cgtaaccacc acaccgccg cgcttaatgc      2040 gccgctacag ggcgcgtcag gtggcacttt tcggggaaat gtgcgcggaa ccctatttg     2100 tttatttttc taaatacatt caaatatgta tccgctcatg agacaataac cctgataaat    2160
gcttcaataa tattgaaaaa ggaagagtcc tgaggcggaa agaaccagct gtggaatgtg    2220
tgtcagttag taatagtaat caattacggg gtcattagtt catagcccat atatggagtt    2280
ccgcgttaca taacttacgg taaatggccc gcctggctga ccgcccaacg accccgccc     2340 attgacgtca ataatgacgt atgttcccat agtaacgcca atagggactt tccattgacg    2400
tcaatgggtg gagtatttac ggtaaactgc ccacttggca gtacatcaag tgtatcatat    2460
gccaagtacg cccccctattg acgtcaatga cggtaaatgg cccgcctggc attatgccca    2520
gtacatgacc ttatgggact ttcctacttg gcagtacatc tacgtattag tcatcgctat    2580
taccatggtg atgcggtttt ggcagtacat caatgggcgt ggatagcggt ttgactcacg    2640
gggatttcca agtctccacc ccattgacgt caatgggagt ttgttttggc accaaaatca    2700
acgggacttt ccaaaatgtc gtaacaactc cgccccattg acgcaaatgg gcggtaggcg    2760
tgtacggtgg gaggtctata taagcagagc tggtttagtg aaccgtcaga tccgctagta    2820
agaaaccatt attatcatga cattaaccta taaaaatagg cgtatacga ggccctttcg     2880 tcttcacctc gagaaatcat aaaaaattta tttgctttgt gagcggataa caattataat    2940
agattcaatt gtgagcggat aacaatttca cacagaattc attaaagagg agaaattaac    3000
tatgagagga tcgcatcacc atcaccatca cggatccgac gaggatggtt cagagggcgg    3060
ccccgccctg ttccagagcg acatgacctt caaaatcttc atcgacggcg aggtgaacgg    3120
ccagaagttc accatcgtgg ccgacggcag cagcaagttc ccccacgcg acttcaacgt     3180 gcacgccgtg tgcgagaccg gcaagctgcc catgagctgg aagcccatct gccacctgat    3240
ccagtacggc gagcccttct cgcccgcta ccccaacggc atcagccact cgcccagga     3300 gtgcttcccc gagggcctga gcatcgaccg caccgtgcgc ttcgagaacg acggcaccat    3360
gaccagccac cacacctacg agctggacgg cacctgcgtg gtcagccgca tcaccgtgaa    3420
ctgcgacggc ttccagcccg acggccccat catgcgcgac cagctggtgg acatcctgcc    3480
caacgagacc cacatgttcc cccacggccc aacgccgtg cgccagctgg ccttcatcgg     3540
cttcaccacc gccgacggcg gcctgatgat gggccacttc gacagcaaga tgaccttcaa    3600
cggcagccgc gccatcaaga tccccggccc ccacttcgtg accatcatca ccaagcagat    3660
gagggacacc agcgacaagc gcgaccacgt gtgccagcgc gaggtgacct acgcccacag    3720
cgtgccccgc atcaccagcg ccatcggtag cgacagagga ggatctcggg tagatatctc    3780
ggccattgaa caagatggat tgcacgcagg ttctccggcc gcttgggtgg agaggctatt    3840
```

```
cggctatgac tgggcacaac agacaatcgg ctgctctgat gccgccgtgt tccggctgtc   3900
agcgcagggg cgcccggttc tttttgtcaa gaccgacctg tccggtgccc tgaatgaact   3960
gcaagacgag gcagcgcggc tatcgtggct ggccacgacg ggcgttcctt gcgcagctgt   4020
gctcgacgtt gtcactgaag cgggaaggga ctggctgcta ttgggcgaag tgccggggca   4080
ggatctcctg tcatctcacc ttgctcctgc cgagaaagta tccatcatgg ctgatgcaat   4140
gcggcggctg catacgcttg atccggctac ctgcccattc gaccaccaag cgaaacatcg   4200
catcgagcga gcacgtactc ggatggaagc cggtcttgtc gatcaggatg atctggacga   4260
agagcatcag gggctcgcgc cagccgaact gttcgccagg ctcaaggcga gcatgcccga   4320
cggcgaggat ctcgtcgtga cccatggcga tgcctgcttg ccgaatatca tggtggaaaa   4380
tggccgcttt tctggattca tcgactgtgg ccggctgggt gtggcggacc gctatcagga   4440
catagcgttg gctacccgtg atattgctga agagcttggc ggcgaatggg ctgaccgctt   4500
cctcgtgctt tacggtatcg ccgctcccga ttcgcagcgc atcgccttct atcgccttct   4560
tgacgagttc ttctgagcgg gactctgggg ttcgaaatga ccgaccaagc gacgcccaac   4620
ctgccatcac gagatttcga ttccaccgcc gccttctatg aaaggttggg cttcggaatc   4680
gttttccggg acgccggctg gatgatcctc cagcgcgggg atctcatgct ggagttcttc   4740
gcccacccta gggggaggct aactgaaaca cggaaggaga caataccgga aggaacccgc   4800
gctatgacgg caataaaaag acagaataaa acgcacggtg ttgggtcgtt tgttcataaa   4860
cgcggggttc ggtcccaggg ctggcactct gtcgataccc caccgagacc ccattggggc   4920
caatacgccc gcgtttcttc cttttcccca ccccaccccc caagttcggg tgaaggccca   4980
gggctcgcag ccaacgtcgg ggcggcaggc cctgccatag cctcaggtta ctcatatata   5040
ctttagattg atttaaaact tcattttaa tttaaaagga tctaggtgaa gatcctttt   5100 gataatctca tgaccaaaat cccttaacgt gagttttcgt tccactgagc gtcagacccc   5160
gtagaaaaga tcaaaggatc ttcttgagat cctttttttc tgcgcgtaat ctgctgcttg   5220
caaacaaaaa aaccaccgct accagcggtg gtttgtttgc cggatcaaga gctaccaact   5280 cttttttccga aggtaactgg cttcagcaga gcgcagatac caaatactgt ccttctagtg   5340
tagccgtagt taggccacca cttcaagaac tctgtagcac cgcctacata cctcgctctg   5400
ctaatcctgt taccagtggc tgctgccagt ggcgataagt cgtgtcttac cgggttggac   5460
tcaagacgat agttaccgga taaggcgcag cggtcgggct gaacggggggg ttcgtgcaca   5520 cagcccagct tggagcgaac gacctacacc gaactgagat acctacagcg tgagctatga   5580
gaaagcgcca cgcttcccga aggagaaag gcggacaggt atccggtaag cggcagggtc   5640
ggaacaggag agcgcacgag ggagcttcca gggggaaacg cctggtatct ttatagtcct   5700
gtcgggtttc gccacctctg acttgagcgt cgatttttgt gatgctcgtc agggggggcgg   5760 agcctatgga aaaacgccag caacgcggcc ttttacggtt cctggccttt tgctggcct   5820 tttgctcaca tgttctttcc tgcgttatcc cctgattctg tggataaccg tattaccgcc   5880
atgcat                                                              5886
```

<210> SEQ ID NO 3  
<211> LENGTH: 22  
<212> TYPE: DNA  
<213> ORGANISM: Artificial  
<220> FEATURE:  
<223> OTHER INFORMATION: Designed oligonucleotide for use as a primer, p13KAN0S01Af12

<400> SEQUENCE: 3
ggcttaaggc gagcatgccc ga                                              22

<210> SEQ ID NO 4
<211> LENGTH: 40
<212> TYPE: DNA
<213> ORGANISM: Artificial
<220> FEATURE:
<223> OTHER INFORMATION: Designed oligonucleotide for use as a primer,
     p5p2FP0A01

<400> SEQUENCE: 4
cgcagcctaa gggcgaattc tatccacaga atcaggggat                           40

<210> SEQ ID NO 5
<211> LENGTH: 40
<212> TYPE: DNA
<213> ORGANISM: Artificial
<220> FEATURE:
<223> OTHER INFORMATION: Designed oligonucleotide for use as a primer,
     p1Pact0S02

<400> SEQUENCE: 5
atcccctgat tctgtggata gaattcgccc ttaggctgcg                           40

<210> SEQ ID NO 6
<211> LENGTH: 40
<212> TYPE: DNA
<213> ORGANISM: Artificial
<220> FEATURE:
<223> OTHER INFORMATION: Designed oligonucleotide for use as a primer,
     p2PactOA02

<400> SEQUENCE: 6
ggcgaccggt agcgctagcg gtggcggccg ccatagacat                           40

<210> SEQ ID NO 7
<211> LENGTH: 40
<212> TYPE: DNA
<213> ORGANISM: Artificial
<220> FEATURE:
<223> OTHER INFORMATION: Designed oligonucleotide for use as a primer,
     p6p2FP0S01

<400> SEQUENCE: 7
atgtctatgg cggccgccac cgctagcgct accggtcgcc                           40

<210> SEQ ID NO 8
<211> LENGTH: 23
<212> TYPE: DNA
<213> ORGANISM: Artificial
<220> FEATURE:
<223> OTHER INFORMATION: Designed oligonucleotide for use as a primer,
     p4Bgl20A01

<400> SEQUENCE: 8
gggagatctt ccgggatcat tct                                             23

<210> SEQ ID NO 9
<211> LENGTH: 23
<212> TYPE: DNA
<213> ORGANISM: Artificial
<220> FEATURE:
<223> OTHER INFORMATION: Designed oligonucleotide for use as a primer,
     p3Bgl20S01

<400> SEQUENCE: 9
gggagatctc gagctcaagc ttc                                             23

```
<210> SEQ ID NO 10
<211> LENGTH: 40
<212> TYPE: DNA
<213> ORGANISM: Artificial
<220> FEATURE:
<223> OTHER INFORMATION: Designed oligonucleotide for use as a primer,
      9P2FP0A01

<400> SEQUENCE: 10
cgcagcctaa gggcgaattc ctaactgaca cacattccac                           40

<210> SEQ ID NO 11
<211> LENGTH: 40
<212> TYPE: DNA
<213> ORGANISM: Artificial
<220> FEATURE:
<223> OTHER INFORMATION: Designed oligonucleotide for use as a primer,
      p7Pact0S01

<400> SEQUENCE: 11
gtggaatgtg tgtcagttag gaattcgccc ttaggctgcg                           40

<210> SEQ ID NO 12
<211> LENGTH: 40
<212> TYPE: DNA
<213> ORGANISM: Artificial
<220> FEATURE:
<223> OTHER INFORMATION: Designed oligonucleotide for use as a primer,
      p8Pact0A01

<400> SEQUENCE: 12
ataatggttt cttactagcg gtggcggccg ccatagacat                           40

<210> SEQ ID NO 13
<211> LENGTH: 40
<212> TYPE: DNA
<213> ORGANISM: Artificial
<220> FEATURE:
<223> OTHER INFORMATION: Designed oligonucleotide for use as a primer,
      p10RFP0S01

<400> SEQUENCE: 13
atgtctatgg cggccgccac cgctagtaag aaaccattat                           40

<210> SEQ ID NO 14
<211> LENGTH: 22
<212> TYPE: DNA
<213> ORGANISM: Artificial
<220> FEATURE:
<223> OTHER INFORMATION: Designed oligonucleotide for use as a primer,
      p14KAN0A01Afl2

<400> SEQUENCE: 14
tcgggcatgc tggccttaag cc                                              22

<210> SEQ ID NO 15
<211> LENGTH: 20
<212> TYPE: DNA
<213> ORGANISM: Artificial
<220> FEATURE:
<223> OTHER INFORMATION: Designed oligonucleotide for use as a primer,
      T3

<400> SEQUENCE: 15
gcaattaacc ctcactaaag                                                 20
```

```
<210> SEQ ID NO 16
<211> LENGTH: 20
<212> TYPE: DNA
<213> ORGANISM: Artificial
<220> FEATURE:
<223> OTHER INFORMATION: Designed oligonucleotide for use as a primer,
      T7

<400> SEQUENCE: 16
taatacgact cactataggg                                              20
```